(12) United States Patent
Burton, Jr.

(10) Patent No.: US 7,820,141 B2
(45) Date of Patent: *Oct. 26, 2010

(54) MOLECULAR SIEVE SSZ-82 COMPOSITION OF MATTER AND SYNTHESIS THEREOF

(75) Inventor: Allen W. Burton, Jr., Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/249,775

(22) Filed: Oct. 10, 2008

(65) Prior Publication Data

US 2009/0060813 A1 Mar. 5, 2009

(51) Int. Cl.
*C01B 39/00* (2006.01)
*C01B 39/02* (2006.01)
*B01J 21/06* (2006.01)

(52) U.S. Cl. .................. 423/704; 423/701; 423/718; 502/100

(58) Field of Classification Search .................. 423/701, 423/704, 718; 502/100; *C01B 39/06*
See application file for complete search history.

(56) References Cited

U.S. PATENT DOCUMENTS

2008/0050308 A1* 2/2008 Vermeiren et al. .......... 423/704

FOREIGN PATENT DOCUMENTS

WO WO 2005/097679 * 10/2005

* cited by examiner

*Primary Examiner*—Jessica L Ward
*Assistant Examiner*—Alexander Polyansky
(74) *Attorney, Agent, or Firm*—Micheal D. Ross; E. Joseph Gess

(57) ABSTRACT

The present invention is directed to a new crystalline molecular sieve designated SSZ-82, a method for preparing SSZ-82 using a 1,6-bis(N-cyclohexylpyrrolidinium) hexane dication as a structure directing agent, and uses for SSZ-82. The molecular sieve has a mole ratio of 20 or greater of (1) an oxide of a first tetravalent element, e.g., silicon oxide to (2) an oxide of a trivalent element, pentavalent element or a second tetravalent element different from the first, e.g., aluminum oxide, gallium oxide, iron oxide, boron oxide, titanium oxide, or indium oxide.

20 Claims, 4 Drawing Sheets

MOLECULAR SIEVE SSZ-82 COMPOSITION OF MATTER AND SYNTHESIS THEREOF

FIELD OF THE INVENTION

The present invention relates to new crystalline molecular sieve SSZ-82, a method for preparing SSZ-82 using a 1,6-bis(N-cyclohexylpyrrolidinium)hexane dication as a structure directing agent ("SDA") and uses for SSZ-82.

BACKGROUND OF THE INVENTION

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY OF THE INVENTION

The present invention is directed to a family of crystalline molecular sieves with unique properties, referred to herein as "molecular sieve SSZ-82" or simply "SSZ-82."

In accordance with the present invention there is provided a molecular sieve having a mole ratio greater than about 20 of (1) an oxide of a first tetravalent element to (2) optionally, an oxide of a trivalent element, pentavalent element, second tetravalent element which is different from the first tetravalent element or a mixture thereof and having, after calcination, the X-ray diffraction lines of Table 6. It should be noted that the phrase "mole ratio greater than about 20" includes the case where there is no oxide (2), i.e., the mole ratio of oxide (1) to oxide (2) is infinity. In that case the molecular sieve is comprised of essentially all of the oxide of the first tetravalent element.

The present invention also includes a method of preparing a crystalline material by contacting under crystallization conditions (1) at least one source of an oxide of a first tetravalent element; (2) one or more sources of an oxide selected from the group consisting of oxides of a trivalent element, a pentavalent element, a second tetravalent element which is different from the first tetravalent element, and mixtures thereof; (3) hydroxide ions; and (4) a 1,6-bis(N-cyclohexylpyrrolidinium)hexane dication.

The present invention also includes a process for preparing a crystalline material having, after calcination, the X-ray diffraction lines of Table 6, by:

(a) preparing a reaction mixture containing (1) at least one source of an oxide of a first tetravalent element; (2) one or more sources of an oxide selected from the group consisting of oxides of a trivalent element, a pentavalent element, a second tetravalent element which is different from the first tetravalent element, and mixtures thereof; (3) at least one active source of an element selected from Groups 1 and 2 of the Periodic Table; (4) hydroxide ions; (5) a 1,6-bis(N-cyclohexylpyrrolidinium)hexane dication, and (6) water; and (b) maintaining the reaction mixture under conditions sufficient to form crystals of the zeolite.

Where the zeolite formed is an intermediate zeolite, the process of the present invention includes a further post-crystallization processing in order to achieve the target zeolite (e.g. by post-synthesis heteroatom lattice substitution or acid leaching).

The present invention also provides SSZ-82 zeolites having a composition, as-synthesized and in the anhydrous state, in terms of mole ratios, as follows:

|  | Broadest | Preferred |
|---|---|---|
| $YO_2/W_cO_d$ | 20-200 | 20-150 |
| $Q/YO_2$ | 0.015-0.05 | 0.015-0.05 |
| $M/YO_2$ | 0-0.04 | 0-0.04 | wherein:

(1) Y is selected from the group consisting of tetravalent elements from Groups 4-14 of the Periodic Table, and mixtures thereof;

(2) W is selected from the group consisting of trivalent, pentavalent and tetravalent elements from Groups 3-13 of the Periodic Table, and mixtures thereof;

(3) stoichiometric variable c is 1 or 2, and d is 2 when c is 1 (i.e., W is tetravalent) or d is 3 or 5 when c is 2 (i.e., d is 3 when W is trivalent or 5 when W is pentavalent);

(4) M is selected from the group consisting of elements from Groups 1 and 2 of the Periodic Table; and (4) Q is an SDA selected from the group consisting of 1,6-bis(N-cyclohexylpyrrolidinium)hexane dications.

DETAILED DESCRIPTION OF THE INVENTION

Introduction

Figure 1:
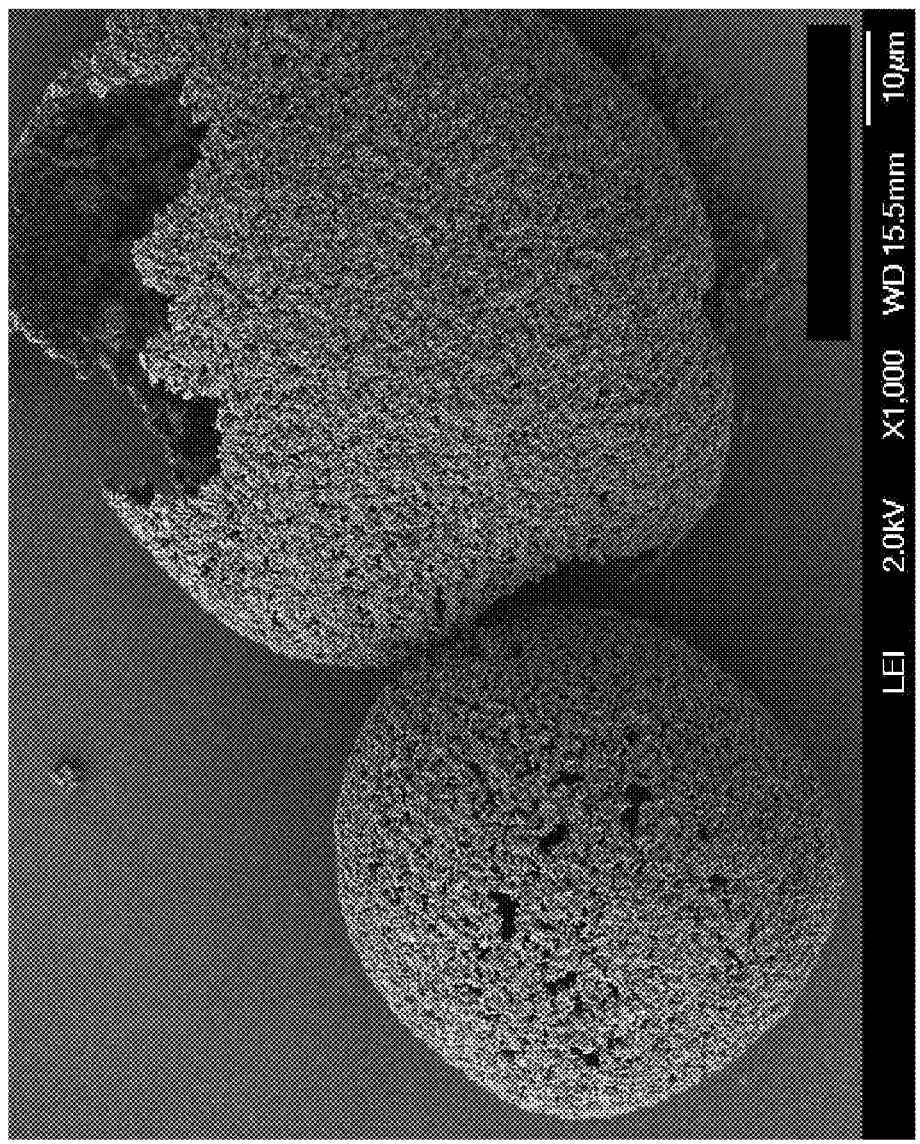
FIG. 1 shows the results of a scanning electron microscopy (SEM) analysis of the zeolite prepared in Example 2.

The term "active source" means a reagent or precursor material capable of supplying an element in a form that can react and be incorporated into the zeolite structure. The terms "source" and "active source" are used interchangeably herein.

The term "Periodic Table" refers to the version of IUPAC Periodic Table of the Elements dated Jun. 22, 2007, and the numbering scheme for the Periodic Table Groups is as described in Chemical and Engineering News, 63(5), 27 (1985).

The term "zeolite" includes (a) intermediate and (b) final or target zeolites produced by (1) direct synthesis or (2) post-crystallization treatment (secondary synthesis). Secondary synthesis techniques allow for the synthesis of a target zeolite from an intermediate zeolite by heteroatom lattice substitution or other techniques. For example, an aluminosilicate can be synthesized from an intermediate borosilicate by post-crystallization heteroatom lattice substitution of the Al for B. Such techniques are known, for example as described in U.S. Pat. No. 6,790,433 to C. Y. Chen and Stacey Zones, issued Sep. 14, 2004.

Where permitted, all publications, patents and patent applications cited in this application are herein incorporated by reference in their entirety, to the extent such disclosure is not inconsistent with the present invention.

Unless otherwise specified, the recitation of a genus of elements, materials or other components, from which an individual component or mixture of components can be selected, is intended to include all possible sub-generic combinations of the listed components and mixtures thereof. Also, "include" and its variants, are intended to be non-limiting, such that recitation of items in a list is not to the exclusion of other like items that may also be useful in the materials, compositions and methods of this invention.

The present invention is directed to a molecular sieve designated herein as "molecular sieve SSZ-82" or simply "SSZ-82."

In preparing SSZ-82, a 1,6-bis(N-cyclohexylpyrrolidinium)hexane dication is used as a structure directing agent ("SDA"), also known as a crystallization template. The SDA useful for making SSZ-82 is represented by the following structure (1):

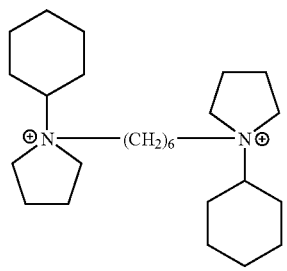

(1)

1,6-bis(N-cyclohexylpyrrolidinium)hexane dication

The SDA dication is associated with anions ($X^-$) which may be any anion that is not detrimental to the formation of SSZ-82. Representative anions include elements from Group 18 of the Periodic Table (e.g., fluoride, chloride, bromide and iodide), hydroxide, acetate, sulfate, tetrafluoroborate, carboxylate, and the like.

The 1,6-bis(N-cyclohexylpyrrolidinium)hexane SDA of the present invention (represented by structure (1) herein) can be synthesized by reacting a dihalidealkane (such as 1,6-dibromobutane) with N-cyclohexylpyrrolidine. In one embodiment, N-cyclohexylpyrrolidine is synthesized by hydrogenation of 1-pyrrolidino-1-cyclohexene. Methods for hydrogenation of 1-pyrrolidino-1-cyclohexene are taught in Example 7 of U.S. Pat. No. 6,544,495 to Saleh Elomari, issued Apr. 8, 2003.

Reaction Mixture

In general, SSZ-82 is prepared by:

(a) preparing a reaction mixture containing (1) at least one source of an oxide of a first tetravalent element; (2) one or more sources of an oxide selected from the group consisting of oxides of a trivalent element, a pentavalent element, a second tetravalent element which is different from the first tetravalent element, and mixtures thereof; (3) at least one active source of an element selected from Groups 1 and 2 of the Periodic Table; (4) hydroxide ions; (5) a 1,6-bis(N-cyclohexylpyrrolidinium)hexane dication; and (6) water; and (b) maintaining the reaction mixture under conditions sufficient to form crystals of the zeolite.

Where the zeolite formed is an intermediate zeolite, the process of the present invention includes a further step of synthesizing a target zeolite by post-synthesis techniques, such as heteroatom lattice substitution techniques and acid leaching.

The composition of the reaction mixture from which the zeolite is formed, in terms of molar ratios, is identified in Table 1 below:

TABLE 1

| Reactants | Broad | Preferred |
|---|---|---|
| $YO_2/W_aO_b$ molar ratio | 8-150 | 10-70 |
| $M/YO_2$ molar ratio | 0.05-0.50 | 0.05-0.30 |
| $Q/YO_2$ molar ratio | 0.05-0.50 | 0.10-0.25 |
| $OH/YO_2$ molar ratio | 0.10-1.0 | 0.20-0.40 |
| $H_2O/YO_2$ molar ratio | 10-200 | 20-60 | wherein:

(a) wherein compositional variables Y, W, Q and M are as described herein above; and (b) a is 1 or 2, and b is 2 when a is 1 (i.e., W is tetravalent) or b is 3 or 5 when a is 2 (i.e., b is 3 when W is trivalent or 5 when W is pentavalent).

In a subembodiment, the composition of the reaction mixture from which SSZ-82 is formed, in terms of molar ratios, is identified in Table 2 below, wherein composition variables Q and M are as described herein above.

TABLE 2

| Reactants | Broad | Preferred |
|---|---|---|
| $SiO_2/B_2O_3$ molar ratio | 8-150 | 10-70 |
| $M/SiO_2$ molar ratio | 0.05-0.50 | 0.05-0.30 |
| $Q/SiO_2$ molar ratio | 0.05-0.50 | 0.10-0.25 |
| $OH/SiO_2$ molar ratio | 0.10-1.0 | 0.20-0.40 |
| $H_2O/SiO_2$ molar ratio | 10-200 | 20-60 |

As noted above, for each embodiment described herein, Y is selected from the group consisting of elements from Groups 4-14 of the Periodic Table. In one subembodiment, Y is selected from the group consisting of germanium (Ge), silicon (Si), and mixtures thereof. In another subembodiment, Y is Si. Sources of elements selected for composition variable Y and the second tetravalent element (represented by composition variable W) include oxides, hydroxides, acetates, oxalates, ammonium salts and sulfates of the element(s) selected for Y and W. In one subembodiment, each active source(s) of the element(s) selected for composition variable Y and W is an oxide. Where Y is Si, sources useful herein for Si include fumed silica, precipitated silicates, silica hydrogel, silicic acid, colloidal silica, tetra-alkyl orthosilicates (e.g. tetraethyl orthosilicate), and silica hydroxides. Sources useful herein for Ge include germanium oxide and germanium ethoxide.

For each embodiment described herein, W is selected from the group consisting of elements from Groups 3-13 of the Periodic Table. In one subembodiment, W is selected from the group consisting of gallium (Ga), aluminum (Al), iron (Fe), boron (B), titanium (Ti), indium (In), and mixtures thereof. In another subembodiment, W is selected from the group consisting of Al, B, Fe, Ga, and mixtures thereof. In another subembodiment, W is Al. In another subembodiment, W is B. Sources of elements selected for optional composition variable W include oxides, hydroxides, acetates, oxalates, ammonium salts and sulfates of the element(s) selected for W. Typical sources of aluminum oxide include aluminates, alumina, and aluminum compounds such as $AlCl_3$, $Al_2(SO_4)_3$, aluminum hydroxide (Al(OH)$_3$)), kaolin clays, and other zeolites. An example of the source of aluminum oxide is LZ-210 zeolite (a type of Y zeolite). Germanium, boron, gallium, titanium and iron can be added in forms corresponding to their aluminum and silicon counterparts.

As described herein above, for each embodiment described herein, the reaction mixture is formed using at least one active source of an element selected from Groups 1 and 2 of the Periodic Table (referred to herein as M). In one subembodiment, the reaction mixture is formed using an active source of an element from Group 1 of the Periodic Table. In another subembodiment, the reaction mixture is formed using an active source of sodium (Na). Any M-containing compound which is not detrimental to the crystallization process is suitable. Sources for such Groups 1 and 2 elements include oxides, hydroxides, nitrates, sulfates, halogenides, oxalates, citrates and acetates thereof.

For each embodiment described herein, the zeolite reaction mixture can be supplied by more than one source. Also, two or more reaction components can be provided by one source. For example, borosilicate zeolites may be synthesized by the method of the present invention using boron-containing beta zeolite as taught in U.S. Pat. No. 5,972,204, issued Oct. 26, 1999 to Corma et al.

The reaction mixture can be prepared either batch wise or continuously. Crystal size, morphology and crystallization time of the crystalline zeolite described herein may vary with the nature of the reaction mixture and the crystallization conditions.

Crystallization and Post-Synthesis Treatment

In practice, the zeolite is prepared by:
(a) preparing a reaction mixture as described herein above; and
(b) maintaining the reaction mixture under crystallization conditions sufficient to form crystals of the zeolite.

The reaction mixture is maintained at an elevated temperature until the crystals of the zeolite are formed. The hydrothermal crystallization is usually conducted under pressure, and usually in an autoclave so that the reaction mixture is subject to autogenous pressure, at a temperature between 125° C. and 200° C.

The reaction mixture may be subjected to mild stirring or agitation during the crystallization step. It will be understood by a person skilled in the art that the zeolites described herein may contain impurities, such as amorphous materials, unit cells having framework topologies which do not coincide with the zeolite, and/or other impurities (e.g., organic hydrocarbons).

During the hydrothermal crystallization step, the zeolite crystals can be allowed to nucleate spontaneously from the reaction mixture. The use of crystals of the zeolite as seed material can be advantageous in decreasing the time necessary for complete crystallization to occur. In addition, seeding can lead to an increased purity of the product obtained by promoting the nucleation and/or formation of the zeolite over any undesired phases. When used as seeds, seed crystals are added in an amount between 1% and 10% of the weight of the source for compositional variable Y used in the reaction mixture.

Once the zeolite crystals have formed, the solid product is separated from the reaction mixture by standard mechanical separation techniques such as filtration. The crystals are water-washed and then dried to obtain the as-synthesized zeolite crystals. The drying step can be performed at atmospheric pressure or under vacuum.

The zeolite can be used as-synthesized, but typically will be thermally treated (calcined). The term "as-synthesized" refers to the zeolite in its form after crystallization, prior to removal of the SDA cation and/or M. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the zeolite. The SDA can also be removed by photolysis techniques (e.g. exposing the SDA-containing zeolite product to light or electromagnetic radiation that has a wavelength shorter than visible light under conditions sufficient to selectively remove the organic compound from the zeolite) as described in U.S. Pat. No. 6,960,327 to Navrotsky and Parikh, issued Nov. 1, 2005.

The zeolite can subsequently be calcined in steam, air or inert gas at temperatures ranging from about 200° C. to about 800° C. for periods of time ranging from 1 to 48 hours, or more. Usually, it is desirable to remove the alkali metal cation (if any) by ion exchange and replace it with hydrogen, ammonium, or any desired metal-ion.

Where the zeolite formed is an intermediate zeolite, the target zeolite can be achieved using post-synthesis techniques such as heteroatom lattice substitution techniques. The target zeolite (e.g. silicate SSZ-82) can also be achieved by removing heteroatoms from the lattice by known techniques such as acid leaching.

The zeolite made from the process of the present invention can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the zeolite can be extruded before drying, or, dried or partially dried and then extruded.

The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa.

SSZ-82 is useful in catalysts for a variety of hydrocarbon conversion reactions such as hydrocracking, dewaxing, olefin isomerization, alkylation of aromatic compounds and the like. SSZ-82 is also useful as an adsorbent for gas separations.

Characterization of the Zeolite

Zeolites made by the process of the present invention have a composition, as-synthesized and in the anhydrous state, as described in Table 3 (in terms of mole ratios), wherein compositional variables Y, W, Q and M and stoichiometric variables c and d are as described herein above:

TABLE 3

|  | Broadest | Preferred |
| --- | --- | --- |
| $YO_2/W_cO_d$ | 20-200 | 20-150 |
| $Q/YO_2$ | 0.015-0.05 | 0.015-0.05 |
| $M/YO_2$ | 0-0.04 | 0-0.04 |

Zeolites made by the process of the present invention have a composition, after receiving secondary synthesis treatment, as described in Table 3 wherein the $YO_2/W_cO_d$ molar ratio is 20-∞.

In one subembodiment, the zeolites made by the process of the present invention have a composition, as-synthesized and in the anhydrous state, as described in Table 4 (in terms of mole ratios), wherein Q and M are as described herein above:

TABLE 4

|  | Broadest | Preferred |
|---|---|---|
| $SiO_2/B_2O_3$ | 20-200 | 20-150 |
| $Q/SiO_2$ | 0.015-0.05 | 0.015-0.05 |
| $M/SiO_2$ | 0-0.04 | 0-0.04 |

Zeolites synthesized by the process of the present invention are characterized by their X-ray diffraction pattern. The X-ray diffraction pattern lines of Table 5 are representative of as-synthesized SSZ-82 made in accordance with this invention. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation and from variations in the Y/W mole ratio from sample to sample. Calcination can also cause minor shifts in the X-ray diffraction pattern. Notwithstanding these minor perturbations, the basic crystal lattice structure remains unchanged.

TABLE 5

Characteristic Peaks for As-Synthesized SSZ-82

| 2 Theta[a] | d-spacing (Angstroms) | Relative Integrated Intensity (%)[b] |
|---|---|---|
| 6.30 | 14.00 | M |
| 7.34 | 12.03 | S |
| 16.48 | 5.38 | VS |
| 18.15 | 4.88 | M |
| 19.36 | 4.58 | VS |
| 20.51 | 4.33 | S |
| 20.83 | 4.26 | S |
| 22.94 | 3.87 | VS |
| 23.36 | 3.80 | VS |
| 23.60 | 3.77 | M |

[a] ±0.20
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

The X-ray diffraction pattern lines of Table 6 are representative of calcined SSZ-82 made in accordance with this invention.

TABLE 6

Characteristic Peaks for Calcined SSZ-82

| 2 Theta[a] | d-spacing (Angstroms) | Relative Integrated Intensity (%)[b] |
|---|---|---|
| 6.27 | 14.08 | VS |
| 7.26 | 12.17 | VS |
| 8.52 | 10.38 | M |
| 9.59 | 9.21 | M |
| 9.92 | 8.91 | S |
| 16.46 | 5.38 | S |
| 19.30 | 4.60 | M |
| 20.78 | 4.27 | M |
| 22.86 | 3.89 | M |
| 23.58 | 3.77 | M |

[a] ±0.20
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

The Powder X-ray diffraction patterns presented herein were collected by standard techniques. The radiation was CuK-α radiation. The peak heights and the positions, as a function of 2θ where θ is the Bragg angle, were read from the relative intensities of the peaks, and d, the interplanar spacing in Angstroms corresponding to the recorded lines, can be calculated.

EXAMPLES

The following examples demonstrate but do not limit the present invention.

Example 1

Synthesis of 1,6-bis(N-cyclohexylpyrrolidinium)hexane Dication

N-cyclohexylpyrrolidine was-synthesized by hydrogenation of 1-pyrrolidino-1-cyclohexene (Sigma-Aldrich) per the teachings in Example 7 of U.S. Pat. No. 6,544,495 to Saleh Elomari, issued Apr. 8, 2003.

In a 250 mL round-bottom flask, 20.0 g cyclohexylpyrrolidine was dissolved in 75 mL acetone. Then, 14.35 g 1,6-dibromohexane was added to the solution. The resultant solution was allowed to sit at room temperature for three weeks. The acetone was then removed by rotoevaporation. The resultant residues were then dissolved in isopropanol and the solution was then intermittently refluxed for 2-3 hour periods over the course of a week. After each refluxing period, the isopropanol was removed and the residues were washed with acetone. The product diquaternary ammonium salt then precipitated as a tan solid. The tan solid was then isolated by vacuum filtration. The resultant solid was then thoroughly rinsed with isopropanol to remove any reactant or monoquaternary products. The product was subsequently rinsed with acetone and then with ethyl ether.

After drying, the purity of the product salt was verified by 1H and 13C NMR. The filtrates were then combined and the refluxing of the isopropanol solutions was repeated to obtain additional product. The purified crops were then combined and ion-exchanged into the hydroxide form by dissolving the salts in water and adding a two-fold excess of AG-1-X8 hydroxide anion-exchange resin (Bio-Rad Laboratories, Inc.) and allowing the exchange to occur overnight. The resin was then removed by filtration and the resultant SDA solution was titrated to determine the hydroxide concentration.

Example 2

4.04 g of a hydroxide solution of 1,6-bis(N-cyclohexylpyrrolidinium)hexane ([OH⁻]=0.45 mmol/g) synthesized per Example 1, 0.72 g 1 N sodium hydroxide, and 3.60 g deionized water were mixed together in a Teflon liner. Then 0.036 g sodium borate decahydrate was dissolved in the solution. Next, 0.54 g CAB-O-SIL M-5 fumed silica (Cabot Corporation) was added to the solution and mixed to create a uniform gel. The liner was then capped and placed within a Parr Steel autoclave reactor. The autoclave was then fixed in a rotating spit (43 rpm) within an oven heated at 160° C. for 21 days. The solid products were recovered from the cooled reactor by vacuum filtration and washed with copious quantities of water.

Figure 2:
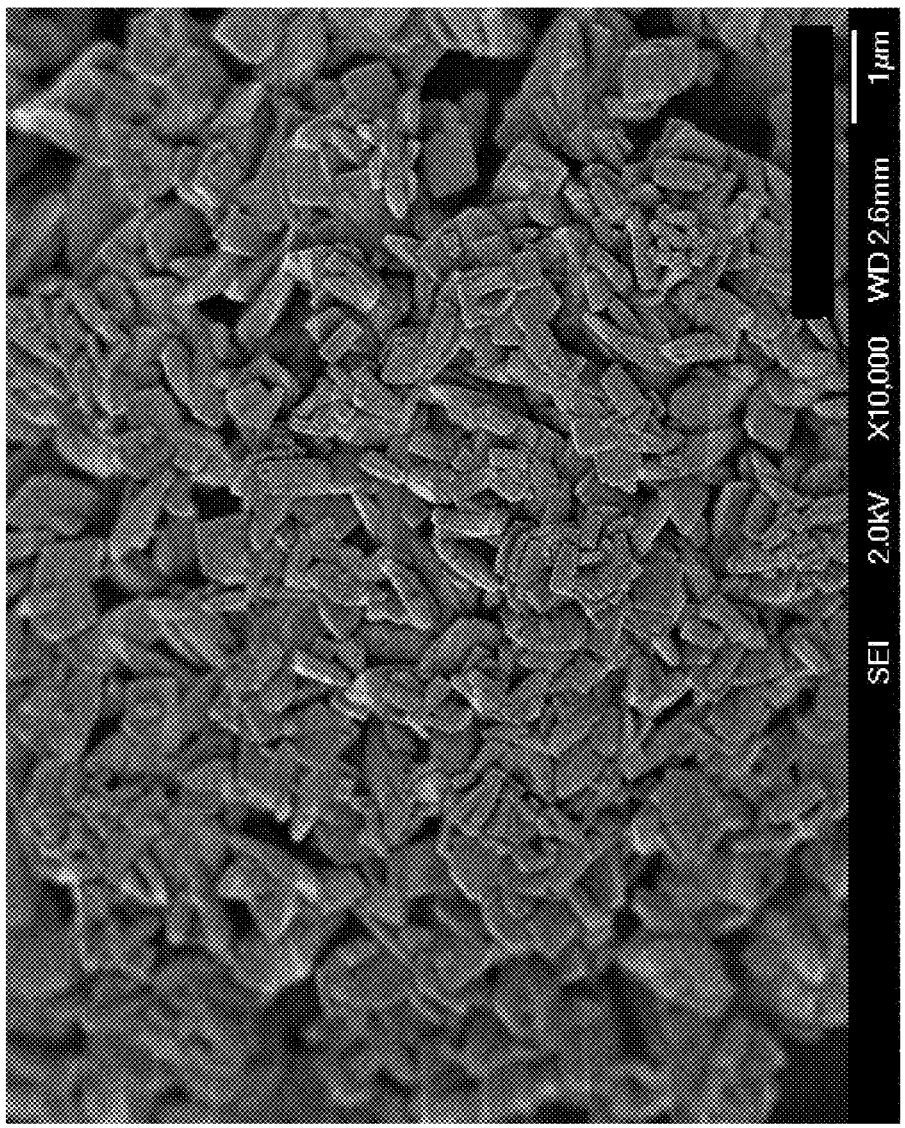
FIG. 2 also shows the results of SEM analysis of the zeolite prepared in Example 2.
Figure 3:
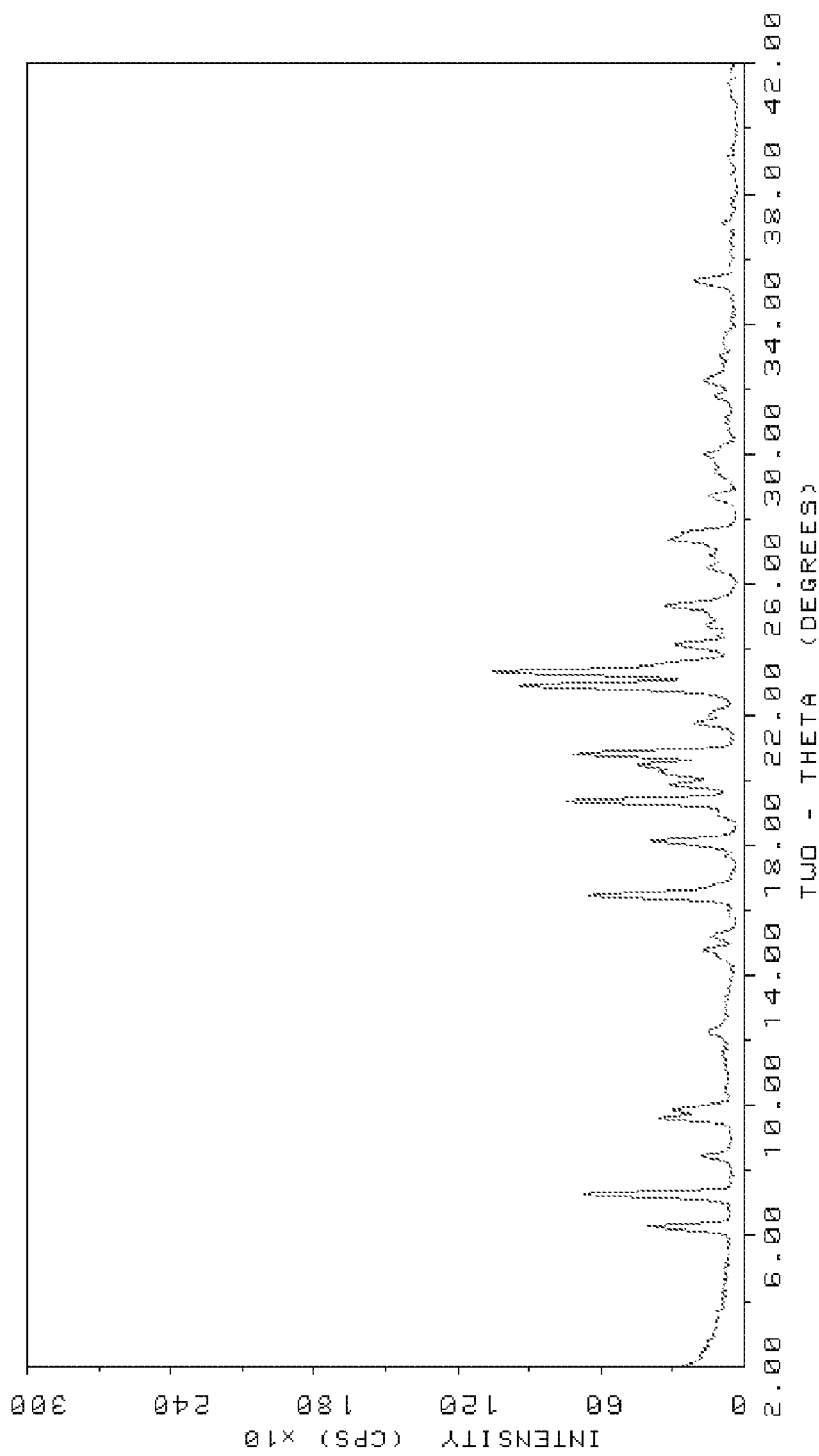
FIG. 3 shows the results of a powder XRD analysis of the zeolite prepared in Example 2.

The resulting zeolite product was analyzed by powder XRD and SEM. The SEM images shown in FIGS. 1 and 2 indicate a uniform field of crystals, and the powder X-ray diffraction shown in FIG. 3 indicates the material was unique. Table 7 below shows the Powder X-ray diffraction lines for the resulting zeolite product.

TABLE 7

| 2 Theta[a] | d-spacing (Angstroms) | Relative Integrated Intensity (%) |
| --- | --- | --- |
| 6.30 | 14.00 | 29.1 |
| 7.34 | 12.03 | 57.5 |
| 8.51 | 10.38 | 8.7 |
| 9.68 | 9.13 | 21.4 |
| 9.93 | 8.90 | 23.9 |
| 12.28 | 7.20 | 7.7 |
| 14.78 | 5.99 | 15 |
| 15.25 | 5.81 | 10.8 |
| 16.48 | 5.38 | 74.8 |
| 18.15 | 4.88 | 36.9 |
| 19.36 | 4.58 | 69.3 |
| 19.90 | 4.46 | 18.7 |
| 20.24 | 4.38 | 13.8 |
| 20.51 | 4.33 | 49.5 |
| 20.83 | 4.26 | 53.6 |
| 21.77 | 4.08 | 12.2 |
| 22.03 | 4.03 | 13.2 |
| 22.21 | 4.00 | 1.5 |
| 22.94 | 3.87 | 96.7 |
| 23.36 | 3.80 | 100 |
| 23.60 | 3.77 | 26.5 |
| 24.22 | 3.67 | 21.5 |
| 24.50 | 3.63 | 2.5 |
| 24.75 | 3.59 | 7.1 |
| 25.02 | 3.56 | 9.4 |
| 25.40 | 3.50 | 41.1 |
| 25.63 | 3.47 | 1.5 |

[a] ±0.20

Example 3

Figure 4:
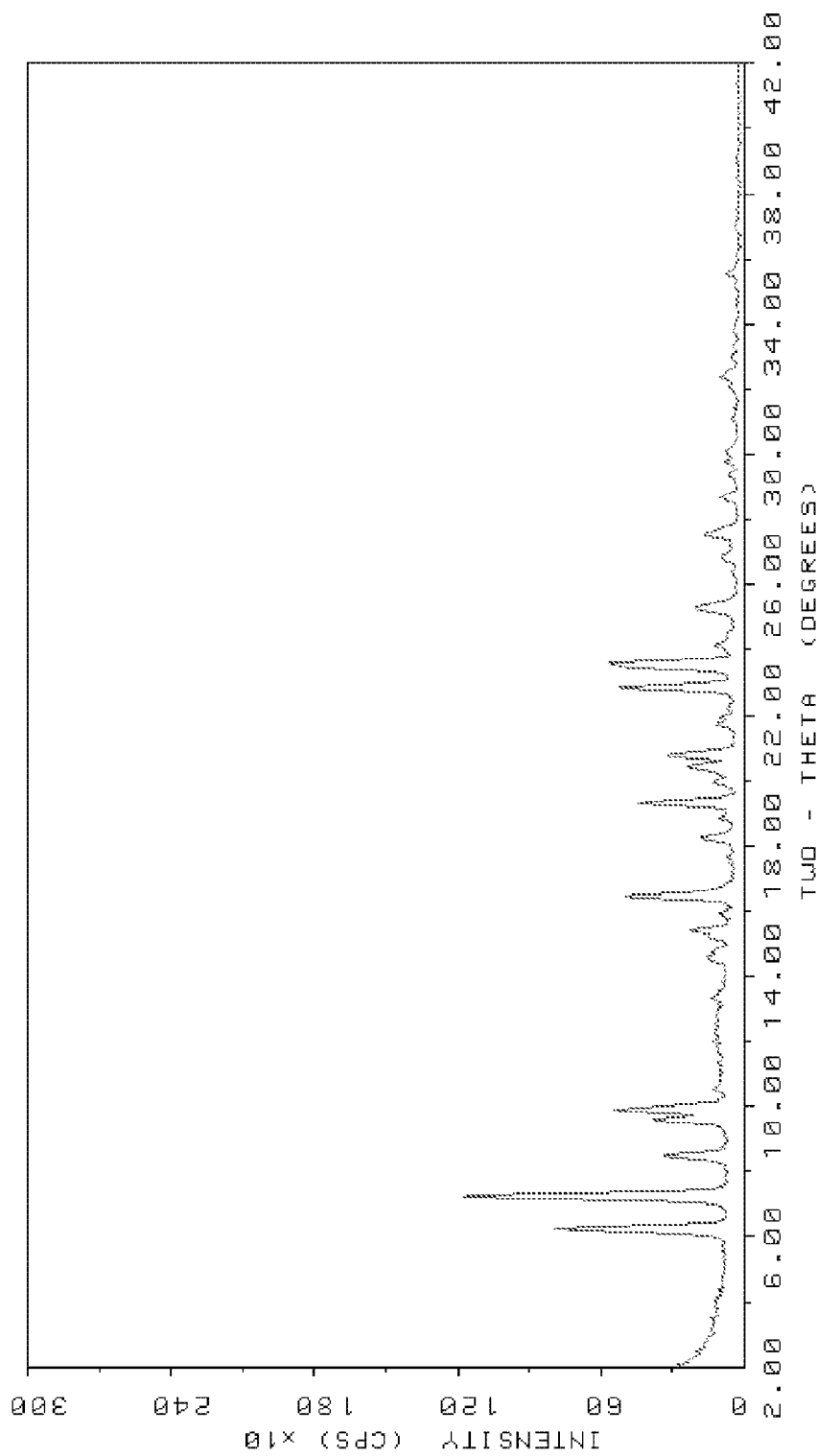
FIG. 4 shows the results of a powder XRD analysis of the zeolite prepared in Example 3.

The solid product from Example 2 was calcined inside a muffle furnace to 595° C. at a rate of 1° C./min and held at 595° C. for five hours. The mass loss after calcination was 19%. The calcined zeolite was analyzed by powder XRD. The powder XRD pattern of the calcined zeolite is shown in FIG. 4 and indicates that the material remains stable after calcination to remove the organic SDA. Table 8 below shows the Powder X-ray diffraction lines for the resulting zeolite product.

TABLE 8

| 2 Theta[a] | d-spacing (Angstroms) | Relative Integrated Intensity (%) |
| --- | --- | --- |
| 6.27 | 14.08 | 63.3 |
| 7.26 | 12.17 | 100 |
| 8.52 | 10.38 | 23.5 |
| 9.59 | 9.21 | 26.4 |
| 9.92 | 8.91 | 42.9 |
| 10.52 | 8.40 | 6.2 |
| 13.42 | 6.59 | 1.2 |
| 14.53 | 6.09 | 8 |
| 14.75 | 6.00 | 1.6 |
| 15.22 | 5.82 | 9.3 |
| 15.43 | 5.74 | 9.5 |
| 15.94 | 5.56 | 2.4 |
| 16.46 | 5.38 | 40.9 |
| 16.67 | 5.31 | 3.7 |
| 17.69 | 5.01 | 1.1 |
| 18.21 | 4.87 | 9.5 |
| 18.29 | 4.85 | 3.1 |
| 18.89 | 4.70 | 3.3 |
| 19.30 | 4.60 | 31.8 |
| 20.00 | 4.44 | 5.9 |
| 20.44 | 4.34 | 20.8 |
| 20.78 | 4.27 | 25.8 |
| 21.74 | 4.08 | 5.2 |
| 21.92 | 4.05 | 2.6 |
| 22.24 | 3.99 | 1.4 |
| 22.79 | 3.90 | 8.1 |
| 22.86 | 3.89 | 31.6 |
| 23.51 | 3.78 | 17.1 |
| 23.58 | 3.77 | 30.4 |
| 24.16 | 3.68 | 6.8 |
| 24.54 | 3.62 | 2.3 |
| 25.30 | 3.52 | 26.8 |
| 26.45 | 3.37 | 1.7 |
| 26.78 | 3.33 | 12.5 |
| 27.57 | 3.23 | 16.3 |
| 27.79 | 3.21 | 1.6 |

[a] ±0.20

Example 4

8.08 g of a hydroxide solution of 1,6-bis(N-cyclohexylpyrrolidinium)hexane ([OH$^-$]=0.45 mmol/g) synthesized per Example 1, 1.44 g 1 N NaOH, and 7.2 g deionized water were mixed together in a Teflon liner. Then 0.072 g sodium borate decahydrate was dissolved in the solution. Next, 1.08 g CAB-O-SIL M-5 fumed silica (Cabot Corporation) was added to the solution and mixed to create a uniform gel. 0.05 g of as-made SSZ-82 seeds (from Example 2) were then added to the gel. The liner was then capped and placed within a Parr Steel autoclave reactor. The autoclave was then fixed in a rotating spit within an oven heated at 160° C. for 10 days. The solid products were recovered from the cooled reactor by vacuum filtration and washed with copious quantities of water. The product zeolite was analyzed by powder XRD and the XRD pattern indicated the material was a pure SSZ-82.

Example 5

2.86 g of a hydroxide solution of 1,6-bis(N-cyclohexylpyrrolidinium)hexane ([OH$^-$]=0.63 mmol/g) synthesized per Example 1, 0.72 g 1 N sodium hydroxide, and 4.78 g deionized water were mixed together in a Teflon liner. Then 0.036 g sodium borate decahydrate was dissolved in the solution. Next 0.54 g CAB-O-SIL M-5 fumed silica (Cabot Corporation) was added to the solution and mixed to create a uniform gel. 0.025 g of as-made SSZ-82 seeds (from Example 4) were then added to the gel. The liner was then capped and placed within a Parr Steel autoclave reactor. The autoclave was then fixed in a rotating spit (43 rpm) within an oven heated at 170° C. for 6 days. The solid products were recovered from the cooled reactor by vacuum filtration and washed with copious quantities of water. The product zeolite was analyzed by powder XRD and the XRD pattern indicated the material was a pure SSZ-82.

Example 6

Example 5 was repeated except all reactants were scaled up by 1.67 times the masses given in Example 5. Four identical preparations were made. The product zeolites were analyzed by powder XRD and the powder XRD patterns indicated the products to be pure SSZ-82.

Example 7

Al-Exchange of B-SSZ-82

The procedure of Example 3 was repeated. The calcined borosilicate form of the zeolite was then converted to the aluminosilicate form following a procedure similar to the procedure described in U.S. Pat. No. 6,790,433 to C. Y. Chen and Stacey Zones, issued Sep. 14, 2004. 5.12 g of aluminum nitrate nonahydrate was dissolved in enough deionized water to create 15 mL of an aluminum nitrate solution. The solution was added to a Teflon liner, and 0.94 g of calcined SSZ-82 zeolite was added to the solution. The liner was then capped and placed within a Parr Steel autoclave reactor. The autoclave was then fixed in a rotating spit (43 rpm) within an oven heated at 160° C. overnight. The solid products were recovered from the cooled reactor by vacuum filtration and washed with copious quantities of water.

Example 8

Constraint Index Determination

The aluminsolicate product of Example 7 was pelletized at 4-5 kpsi and crushed and meshed to 2040. 0.50 g was packed into a ⅜ inch stainless steel tube with alundum on both sides of the zeolite bed. A Lindburg furnace was used to heat the reactor tube. Helium was introduced into the reactor tube at 10 cc/min. and at atmospheric pressure. The reactor was heated to about 316° C., and a 50/50 (w/w) feed of n-hexane and 3-methylpentane is, introduced into the reactor at a rate of 8 μL/min. Feed delivery is made via a Brownlee pump. Direct sampling into a gas chromatograph begins after 10 minutes of feed introduction. The Constraint Index value (not including 2-methylpentane) was calculated from the gas chromatographic data using methods known in the art, and was found to be between 0.56 and 0.49 for times on stream from 10 to 100 minutes. At 316° C. and 10 minutes on-stream, feed conversion was greater than 73%. After 100 minutes on stream the conversion was 35%.

Example 9

Example 4 was repeated except double the amount of sodium borate decahydrate was used (0.072 g), only 0.02 g of seeds from Example 4 were used, and the synthesis was performed at 170° C. for 6 days. Powder XRD indicated the product to be pure SSZ-82. The product had an Si/B ratio of 28.1 by ICP analyses.

Example 10

4.77 g of a hydroxide solution of 1,6-bis(N-cyclohexylpyrrolidinium)hexane ([OH$^-$]=0.63 mmol/g), 1.20 g 1 N sodium hydroxide, and 7.97 g deionized water were mixed together in a Teflon liner. Then 0.12 g sodium borate decahydrate and 0.076 g boric acid were dissolved in the solution. Next 0.90 g CAB-O-SIL M-5 fumed silica (Cabot Corporation) was added to the solution and mixed to create a uniform gel. 0.033 g of as-made SSZ-82 seeds (from Example 4) were then added to the gel. The liner was then capped and placed within a Parr Steel autoclave reactor. The autoclave was then fixed in a rotating spit (43 rpm) within an oven heated at 170° C. for 24 days. The solid products were recovered from the cooled reactor by vacuum filtration and washed with copious quantities of water. Powder X-ray diffraction indicated the material was pure SSZ-82

Example 11

Example 4 was repeated except 0.11 g sodium borate decahydrate was used instead of 0.036 g sodium borate decahydrate, 0.02 g seeds from Example 4 were used, and the synthesis was performed at 170° C. for 7 days. Powder XRD indicated the product to be pure SSZ-82. The product had an Si/B ratio of 24.4 as determined by ICP analyses.

Example 12

Example 11 was repeated except 0.15 g sodium borate decahydrate were used in the synthesis, and the synthesis was performed at 170° C. for 14 days. Powder XRD indicated the product to be pure SSZ-82. The product had an Si/B ratio of 19.2 as determined by ICP analyses.

Example 13

222.0 g of a hydroxide solution of 1,6-bis(N-cyclohexylpyrrolidinium)hexane ([OH$^-$]=0.60 mmol/g), 48.1 g 1 N sodium hydroxide, and 364.1 g deionized water were mixed together in a Teflon liner insert for a 1-L steel Parr autoclave reactor equipped with an overhead stirrer. Next 8.14 g sodium borate decahydrate was dissolved in the solution, and then 39.96 g CAB-O-SIL M-5 fumed silica (Cabot Corporation) was mixed into the solution to create a uniform suspension. 1.0 g zeolite seeds (prepared according to the procedure in Example 10) were added to the gel. The liner was then sealed within the Parr Steel autoclave reactor. The overhead stirrer spun at a rate of 200 rpm. The autoclave was heated to 170° C. over an 8-hr period and then allowed to remain at 170° C. for 7 days. The solid products were recovered from the cooled reactor by vacuum filtration and washed with copious quantities of water. The solids were then allowed to dry in an oven at 95° C. for over 12 hours. The powder X-ray diffraction indicated the product was pure SSZ-82.

What is claimed is:

1. A molecular sieve having a mole ratio of 20 or greater of (1) an oxide of a first tetravalent element to (2) an oxide of a trivalent element, pentavalent element, second tetravalent element which is different from the first tetravalent element or a mixture thereof and having, after calcination, an X-ray diffraction pattern substantially as shown in the following Table:

| 2 Theta | d-spacing (Angstroms) | Relative Integrated Intensity (%) |
|---|---|---|
| 6.27 ± 0.2 | 14.08 | VS |
| 7.26 ± 0.2 | 12.17 | VS |
| 8.52 ± 0.2 | 10.38 | M |

-continued

| 2 Theta | d-spacing (Angstroms) | Relative Integrated Intensity (%) |
|---|---|---|
| 9.59 ± 0.2 | 9.21 | M |
| 9.92 ± 0.2 | 8.91 | S |
| 16.46 ± 0.2 | 5.38 | S |
| 19.30 ± 0.2 | 4.60 | M |
| 20.78 ± 0.2 | 4.27 | M |
| 22.86 ± 0.2 | 3.89 | M |
| 23.58 ± 0.2 | 3.77 | M. |

2. The molecular sieve according to claim 1, wherein the molecular sieve has a mole ratio of 20 or greater of (1) silicon oxide to (2) an oxide selected from aluminum oxide, gallium oxide, iron oxide, boron oxide, titanium oxide, indium oxide and mixtures thereof.

3. The molecular sieve according to claim 1, wherein the molecular sieve has a composition, as-synthesized and in the anhydrous state, in terms of mole ratios, as follows:

| | |
|---|---|
| $YO_2/W_cO_d$ | 20-200 |
| $Q/YO_2$ | 0.015-0.05 |
| $M/YO_2$ | 0-0.04 | wherein:
(1) Y is selected from the group consisting of tetravalent elements from Groups 4-14 of the Periodic Table, and mixtures thereof;
(2) W is selected from the group consisting of trivalent, pentavalent and tetravalent elements from Groups 3-13 of the Periodic Table, and mixtures thereof;
(3) M is selected from the group consisting of elements from Groups 1 and 2 of the Periodic Table; and
(4) Q is an SDA selected from the group consisting of 1,6-bis(N-cyclohexylpyrrolidinium)hexane dications.

4. The molecular sieve according to claim 3, wherein Y is selected from the group consisting of Ge, Si, and mixtures thereof.

5. The molecular sieve according to claim 4, wherein Y is Si.

6. The molecular sieve according to claim 4, wherein W is selected from the group consisting of Ga, Al, Fe, B, Ti, In, and mixtures thereof.

7. The molecular sieve according to claim 6, wherein W is selected from the group consisting of Al, B, Fe, Ga, and mixtures thereof.

8. The molecular sieve according to claim 3, wherein W is selected from the group consisting of Ga, Al, Fe, B, Ti, In, and mixtures thereof.

9. The molecular sieve according to claim 8, wherein W is selected from the group consisting of Al, B, Fe, Ga, and mixtures thereof.

10. The molecular sieve according to claim 3; wherein Y is Si and W is B.

11. A method of preparing a molecular sieve comprising contacting under crystallization conditions (1) at least one source of an oxide of a first tetravalent element; (2) one or more sources of an oxide selected from the group consisting of oxides of a trivalent element, a pentavalent element, a second tetravalent element which is different from the first tetravalent element, and mixtures thereof; (3) hydroxide ions; and (4) a 1,6-bis(N-cyclohexylpyrrolidinium)hexane dication.

12. The method of claim 11, wherein the molecular sieve is prepared from a reaction mixture comprising, in terms of mole ratios, the following

| | |
|---|---|
| $YO_2/W_aO_b$ | 8-150 |
| $M/YO_2$ | 0.05-0.50 |
| $Q/YO_2$ | 0.05-0.50 |
| $OH/YO_2$ | 0.10-1.0 |
| $H_2O/YO_2$ | 10-200 | wherein:
(1) Y is selected from the group consisting of tetravalent elements from Groups 4-14 of the Periodic Table, and mixtures thereof;
(2) W is selected from the group consisting of trivalent, pentavalent and tetravalent elements from Groups 3-13 of the Periodic Table, and mixtures thereof;
(3) M is selected from the group consisting of elements from Groups 1 and 2 of the Periodic Table; and
(4) Q is an SDA selected from the group consisting of 1,6-bis(N-cyclohexylpyrrolidinium)hexane dications.

13. The method according to claim 12, wherein Y is selected from the group consisting of Ge, Si, and mixtures thereof.

14. The method according to claim 13, wherein Y is Si.

15. The method according to claim 13, wherein W is selected from the group consisting of Ga, Al, Fe, B, Ti, In, and mixtures thereof.

16. The method according to claim 15, wherein W is selected from the group consisting of Al, B, Fe, Ga, and mixtures thereof.

17. The method according to claim 12, wherein W is selected from the group consisting of Ga, Al, Fe, B, Ti, In, and mixtures thereof.

18. The method according to claim 17, wherein W is selected from the group consisting of Al, B, Fe, Ga, and mixtures thereof.

19. The method according to claim 11, wherein Y is Si and W is B.

20. The method according to claim 11, wherein the molecular sieve has, after calcination, an X-ray diffraction pattern substantially as shown in the following Table:

| 2 Theta | d-spacing (Angstroms) | Relative Integrated Intensity (%) |
|---|---|---|
| 6.27 ± 0.2 | 14.08 | VS |
| 7.26 ± 0.2 | 12.17 | VS |
| 8.52 ± 0.2 | 10.38 | M |
| 9.59 ± 0.2 | 9.21 | M |
| 9.92 ± 0.2 | 8.91 | S |
| 16.46 ± 0.2 | 5.38 | S |
| 19.30 ± 0.2 | 4.60 | M |
| 20.78 ± 0.2 | 4.27 | M |
| 22.86 ± 0.2 | 3.89 | M |
| 23.58 ± 0.2 | 3.77 | M. |

* * * * *